United States Patent [19]

Dunn

[11] Patent Number: 5,776,737
[45] Date of Patent: Jul. 7, 1998

[54] METHOD AND COMPOSITION FOR INTERNAL IDENTIFICATION OF SAMPLES

[75] Inventor: James M. Dunn, Scarborough, Canada

[73] Assignee: Visible Genetics Inc., Toronto, Canada

[21] Appl. No.: 361,757

[22] Filed: Dec. 22, 1994

[51] Int. Cl.$^6$ .............................. C12P 19/34; C12Q 1/68; C12Q 1/70; C07M 21/04

[52] U.S. Cl. ........................ 435/91.1; 435/91.2; 435/6; 435/5; 435/174; 435/173.1; 435/172.3; 435/320.1; 435/252.3; 536/24.3; 536/24.33; 536/24.32; 250/458.1

[58] Field of Search .......................... 435/91.1, 91.2, 435/6, 5, 174, 173.1, 172.3, 320.1, 252.3; 536/24.3; 250/458.1

[56] References Cited

U.S. PATENT DOCUMENTS

| | | | |
|---|---|---|---|
| 5,139,812 | 8/1992 | Lebacq | 427/7 |
| 5,451,505 | 9/1995 | Dollinger | 435/6 |
| 5,491,225 | 2/1996 | Picone et al. | 536/24.32 |
| 5,650,274 | 7/1997 | Kambara et al. | 435/6 |

FOREIGN PATENT DOCUMENTS

| | | |
|---|---|---|
| 0408424 | 1/1991 | European Pat. Off. . |
| 87/06383 | 10/1987 | WIPO . |
| 90/14441 | 11/1990 | WIPO . |
| 91/17265 | 11/1991 | WIPO . |
| 94/04918 | 3/1994 | WIPO . |
| WO94/0851 | 4/1994 | WIPO . |
| WO/9411530 | 5/1994 | WIPO . |
| WO9413623 | 6/1994 | WIPO . |

OTHER PUBLICATIONS

Bhat. Gene 134:83–87, 1993.

*Primary Examiner*—W. Gary Jones
*Assistant Examiner*—Dianne Rees
*Attorney, Agent, or Firm*—Oppedahl & Larson

[57] ABSTRACT

Patient samples are identified by adding to the sample, preferably at the time it is taken, a plurality of identification oligonucleotides. The identification oligonucleotides are co-processed and sequenced at the same time as the sample. The resulting sequence analysis thus provides both the sequence of the region of interest in the sample DNA, and the sequence of the identification oligonucleotides which are used to confirm the identity of the patient. In an embodiment of the invention, a plurality of specially constructed identification oligonucleotides is used. Each identification oligonucleotide is constructed based upon a starting oligonucleotide and comprises (a) a primer site which is not homologous with DNA from the organism from which the sample is taken and which may be the same or different from the primer site of the other identification oligonucleotides; and (b) an identification region having the general formula $$\text{-(M-N)}_x\text{- or -(M-N-N)}_x\text{-}$$

wherein N represents a nucleotide residue which is the same in the identification oligonucleotide as in the starting oligonucleotide. M represents a nucleotide residue which may be the same as or different from the starting oligonucleotide, with the proviso that at least one M residue in the identification region is different from the starting oligonucleotide, and x is an integer from 3 to 20. To ensure that there is no overlap between different sets of identification oligonucleotides, the identification oligonucleotides may be constructed such that the identification regions of each set are located at a different place along the starting oligonucleotide.

19 Claims, 3 Drawing Sheets

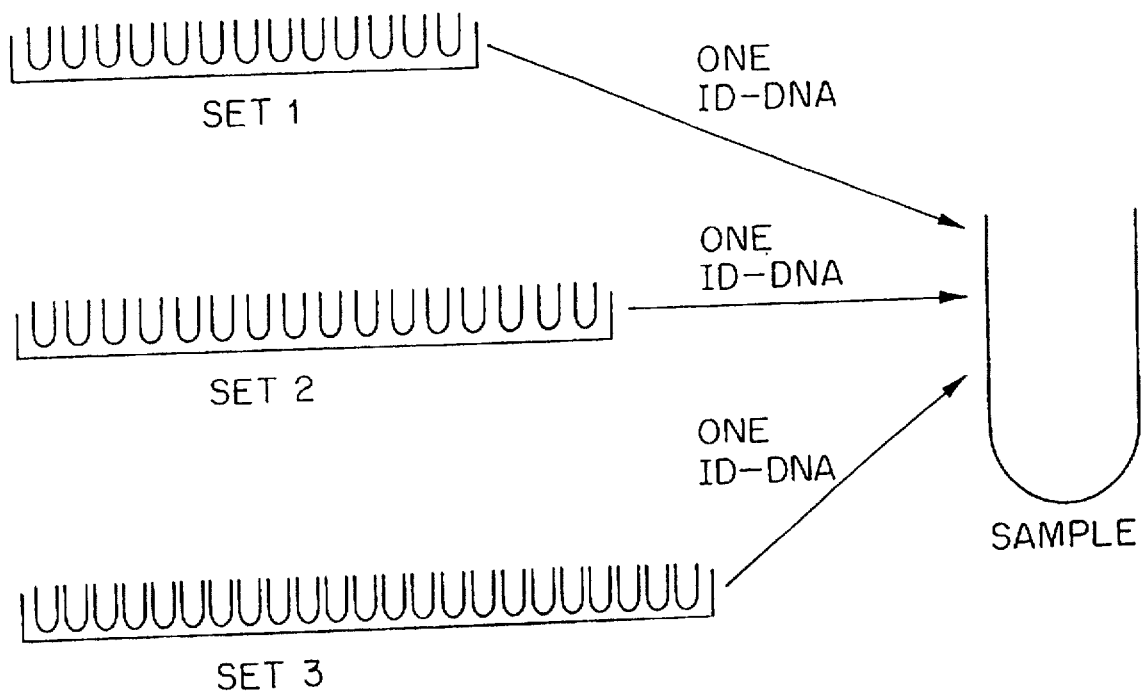
FIG. 1
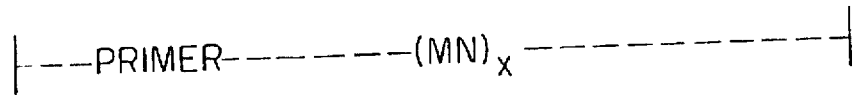
FIG. 2
PRIMER A
N N N N N N (M N) (M N) (M N) (M N) (M N) N N N N
M =   A      A      A      A      A
      C      C      C      C      C
      G      G      G      G      G
      OR     OR     OR     OR     OR
      T      T      T      T      T
N = NUCLEOTIDE CAPABLE OF HYBRIDIZING WITH
CORRESPONDING NUCLEOTIDE AT PRIMER A BINDING SITE.
TOTAL NUMBER OF VARIANT SPECIES: $4^5 = 1024$
FIG. 4

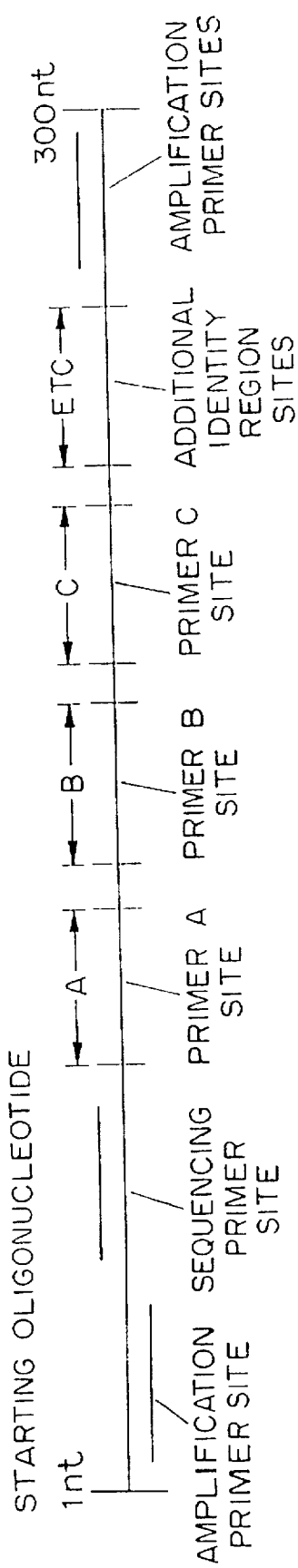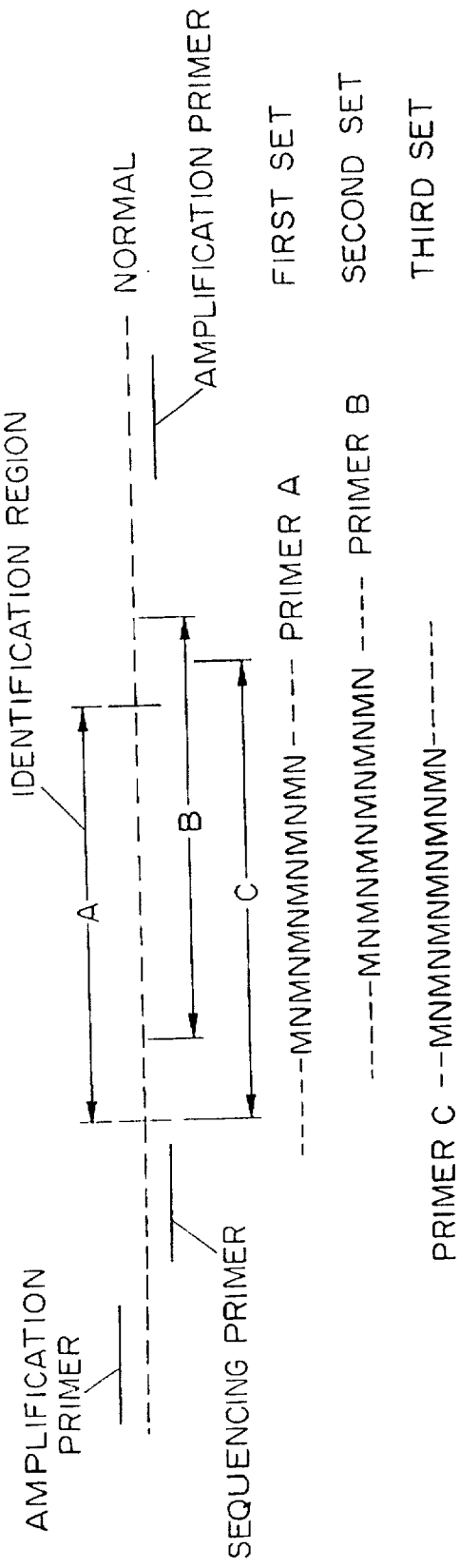

5,776,737

METHOD AND COMPOSITION FOR INTERNAL IDENTIFICATION OF SAMPLES

BACKGROUND OF THE INVENTION

This application relates to a method and compositions for providing internal identification in samples, and particularly in samples for nucleic acid sequencing.

With the advent of nucleic acid amplification procedures such as PCR, and the identification of increasing numbers of disease-associated mutations, the importance of nucleic acid sequence analysis of a patient sample is increasing. Indeed, some persons involved in diagnostics have suggested that complete identification of a DNA sequence is the only appropriate methodology for diagnostic genetic testing.

There are various methods known for the determining the sequence of genetic material derived from a patient sample, including those described in U.S. Pat. Nos. 4,811,218; 4,823,007; 5,062,942; 5,091,652; 5,119,316 and 5,122,345, which are incorporated herein by reference. In general, these tests all require the transfer of materials from the container in which the sample was collected to at least one other container. Thus, even where the original sample container is correctly labeled there is a risk that samples taken from different patients will be mixed up during the subsequent transfers for analysis.

It is an object of the present invention to provide a method for internal identification of patient samples which will be used for nucleic acid sequencing test procedures.

It is a further object of the present invention to provide compositions useful for providing internal identification of patient samples which will be used for nucleic acid sequencing test procedures.

It is a further object of the present invention to provide a method of making compositions useful for providing internal identification of patient samples which will be used for nucleic acid sequencing test procedures.

SUMMARY OF THE INVENTION

In accordance with the present invention, patient samples are identified by adding to the sample, preferably at the time it is taken, a plurality of identification polynucleotides. The identification polynucleotides are co-processed and sequenced at the same time as the sample. The resulting sequence analysis thus provides both the sequence of the region of interest in the sample DNA, and the sequence of the identification polynucleotides which are used to confirm the identity of the patient.

In a preferred embodiment of the invention, a plurality of specially constructed identification polynucleotides is used. Each identification polynucleotide is costructed based upon a starting polynucleotide and comprises (a) a primer site which is not homologous with DNA from the organism from which the sample is taken and which may be the same or different from the primer site of the other identification polynucleotides; and (b) an identification region having the general formula

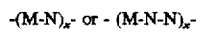

wherein N represents a nucleotide residue which is the same in the identification polynucleotide as in the starting polynucleotide, M represents a nucleotide residue which may be the same as or different from the starting polynucleotide, with the proviso that at least one M residue in the identification region is different from the starting polynucleotide, and x is an integer from 3 to 20. The identification polynucleotides may be constructed such that the identification regions of each set are located at a different place along the starting polynucleotides.

BRIEF DESCRIPTION OF THE DRAWINGS

FIG. 1 shows the basic strategy of the present invention;

FIG. 2 shows a schematic representation of an identification polynucleotide according to the invention;

FIG. 3 shows schematic representation of a starting nucleotide with several non-overlapping primer sites marked;

FIG. 4 shows a structure of a heterogeneous primer useful in the invention;

FIG. 5. Shows a schematic representation of several sets of identification polynucleotides having overlapping identification regions.

DETAILED DESCRIPTION OF THE INVENTION

Figure 6:
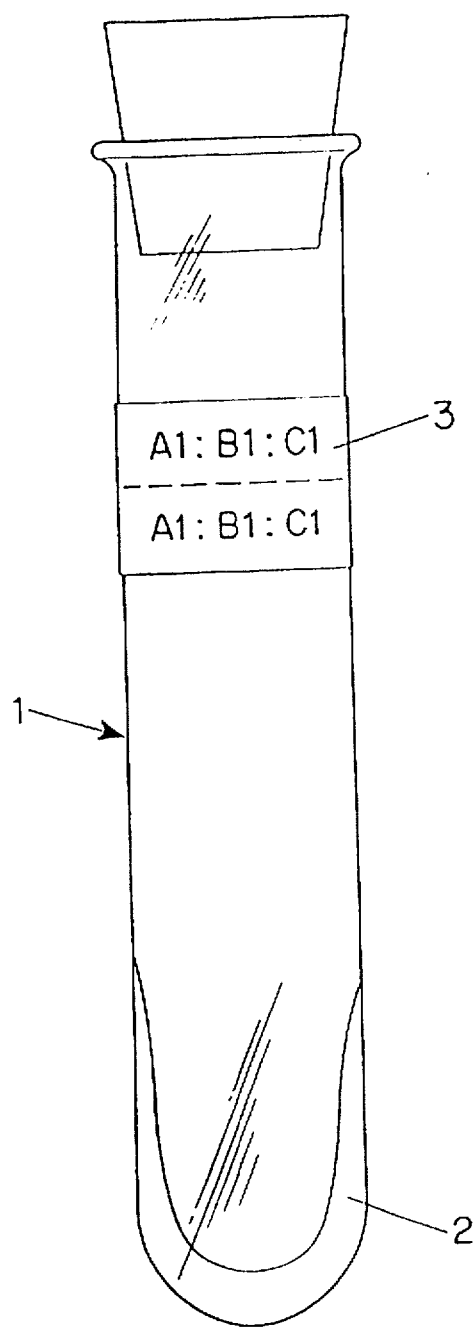
FIG. 6 shows a vessel in accordance with the invention for taking samples.

The object of the present invention is to provide an internal reference which allows for the unambiguous labeling of patient samples which are processed to determine the sequence of nucleic acid polymers in the sample. This object is fulfilled by the addition to the sample of a plurality of identification polynucleotides, preferably at the time of sample collection. The identification polynucleotides are subsequently sequenced to identify the sample.

While any unique polynucleotide could, in principle, be used as an identification polynucleotide, the cost associated with synthesizing large numbers of unique nucleotides is likely to be prohibitive. Thus, it would be desirable to have a method of introducing a large numbers of unique identifiers based upon a collection of standard identification polynucleotides.

FIG. 1 shows the basic strategy of the present invention. A plurality of sets of identification polynucleotides is provided. Each member of a set is different from the other members of that set, and each set is clearly distinct from other sets. One identification polynucleotide (or "ID-DNA") is selected from each set and placed in the sample. Identifying which members of the sets are in a sample provides a positive confirmation of the source of the sample.

One possible construction of an identification polynucleotide is shown in FIG. 2. The polynucleotide has a primer region, indicated as "Primer" and an identification region, indicated as "$(MN)_x$," where N represents a nucleotide residue which is the same in all members of the set, and M represent a nucleotide residue which is variable. The identification polynucleotides within a given set differ in the structure of the identification region as a result of variations in the M residues, and are otherwise the same. Identification polynucleotides in different sets have the same general structure, but are selected to preclude the existence of identical species in two different sets, for example by varying the structure of the primer region, or the position of the identification region relative to the primer, or both.

To illustrate the power of this approach, consider the use of three sets of identification polynucleotides of the type shown in FIG. 2, where x in the identification region is 4. Because there are four possible bases (A,T,G and C) at each of the four M locations, there are a total of 256 ($4^4$) possible polynucleotides within each set. Using three sets of 256 polynucleotides as shown in FIG. 1 to identify the sample, there are a total of over 16 million ($256^3$) different combinations which can be made to identify a particular sample.

The selection of three sets in FIG. 1 is merely an example of one embodiment of the invention. The number of sets used to identify a sample in accordance with the method of the invention must be at least two in order to avoid the problem of having to synthesize a unique identification polynucleotide for each sample to be identified. In principle, any larger number of sets can be employed although as a practical matter use of too many sets will impose a greater sequencing burden than can be reasonably justified. Thus, for reasons of practicality, the preferred number of sets is from 3 to 6, with 3 to 4 sets being most preferred.

The value of x in the structure shown in FIG. 2 determines the number of different polynucleotides within a set, this number being equal to $4^x$. The value of x should be at least 2, but is preferably from 3 to 20, more preferably 4 to 16. Where x is large, for example at least 8 to 10, it provides for 65,000 to over a million possible polynucleotides within the set. While isolation of all of these polynucleotides is neither necessary nor realistic, the existence of so many possibilities makes the isolation of a set of reasonable size, i.e. from 20 to 256 different polynucleotides easier.

It should also be recognized that the structure shown in FIG. 2 for the identification region, i.e., $(MN)_x$, is not the only possible configuration. For example, an alternative structure might utilize a identification regions having the structure $(MNN)_x$. Other identification regions in which an appropriate number of variations are introduced in a less regular pattern might also be used without departing from the spirit and teaching of the present invention.

The process of preparing identification polynucleotides according to the invention can be performed in any of a number of ways. For example, identification regions could be prepared by chemical synthesis in the desired patterns using any of a number of chemical synthesis methods, such as solid phase synthesis. Such identification regions could be ligated into the remainder of the identification polynucleotide to create a population of molecules of which each member can be independently amplified and purified to produce adequate supplies of each member of the set.

An alternative and preferred method for preparing sets of identification polynucleotides makes use of site directed mutagenesis and clonal amplification to prepare multiple members of the set, which are then isolated from one another to provide the sets of identification polynucleotides for use in the invention. In this approach, a starting polynucleotide, which will be the target for site-directed mutagenesis, is selected. The starting polynucleotide should be about 100 to 600 base pairs in size, and preferably around 300 base pairs and derived from a non-mammalian source such as a virus or an insect. This starting polynucleotide is part of, or is cloned into, any vector which produces single stranded copies of the plasmid in quantities suitable for isolation. As such, the starting polynucleotide may be part of a virus such as M13. Alternatively, the starting polynucleotide may be cloned into any plasmid vector which contains the F1 origin of replication such as pEMBL 18, such that when grown in the presence of active F1 phage single stranded copies of the plasmid may be isolated.

FIG. 3 shows a starting polynucleotide including several non-overlapping primer sites. Multiple sets of identification polynucleotides are prepared through site-directed mutagenesis using single stranded copies as templates, as follows. To prepare a first set, a Primer A is annealed at a first location on the single stranded template and extended, for example using the Klenow fragment of DNA polymerase I in the presence of dNTPs and suitable buffer. Primer A is actually a heterogeneous and highly variable population of molecules constructed as illustrated in FIG. 4. The variation in the primer structure may be achieved during solid state synthesis of nucleotides by adding equal amounts of each dNTP amidite for insertion at each site labeled M in FIG. 4.

Each member of the Primer A population contains a sufficient number of nucleotides on the 5' and 3' end of the molecule to ensure that hybridization to the Primer A site will occur with high specificity regardless of the number of potential mismatch sites (M) which are in fact mismatched in any given primer. The resulting double stranded DNA is used to transform bacteria and plated to allow isolation of single colonies.

This procedure may be repeated to create a second set of identification polynucleotides on a new sample of the same single stranded vector DNA using Primer B which primer also consists of a highly variable population of molecules constructed as illustrated in FIG. 4. A third set may be created using Primer C, and so on for as many sets as are desired.

Purified samples of each identification polynucleotide may be obtained from plated transformed bacteria as follows. If the DNA is transformed into *E. coil* which is subsequently grown on Luria Broth plates, single colonies may be picked and mini-prepped. A mini-prep consists of growing a small culture (1–2 mls) of bacteria in a media conducive to bacterial growth such as Luria Broth. The cells are collected by centrifugation and the supernatant is discarded. The cells are resuspended in 100 microliters of a cold solution of buffered glucose containing 1 microgram per microliter lysozyme. Once cells are completely resuspended, 200 microliters of a solution containing 0.2N NaOH and 1% SDS (sodium dodecyl sulphate, by weight) are added and gently mixed. The sample is cooled on ice, and then mixed with 150 microliters of ice cold 5M acetate pH about 3–4. The sample is mixed gently, and the precipitate is spun down. The supernatant is removed and saved. To the supernatant is added 2 volumes of ice cold 100% ethanol, and the sample is mixed. Plasmid DNA is pelleted by centrifugation and resuspended in a buffered solution and stored at 4° C. (See Maniatis, 1.25–1.28).

Because the site-directed mutagenesis technique may result in a mixed population of molecules within one bacteria, it is often necessary to take plasmid DNA from the first mini-prep and retransform it into another population of competent cells. New transformants generally carry only a homozygous population of plasmids. These new transformants may be plated, grown up and mini-prepped to obtain a single population of purified DNAs.

Homozygous mini-prepped DNA from each final isolate may be sequenced to determine the variation present in the particular sample. This technique allows rapid classification of plasmids. 20–256 host organisms each transformed with an polynucleotide containing a different identification region are preferably selected to make up each set.

To prepare DNA for use as identification polynucleotides, the selected organisms are cultured, and DNA is maxi-prepped. A maxi-prep is a large scale version of the mini-prep which generally results in larger amounts of more highly purified DNA, by proportional scale up of volumes. In addition, the ethanol precipitation step is replaced with a 0.6 vol. isopropyl alcohol precipitation step (see Maniatis, 2nd ed. 1.33–1.38.). After resuspension, DNA is purified on a CsCl gradient (see Maniatis, 2nd ed. 1.42–1.46.) Maniatis, "Molecular Cloning", A Laboratory Manual, 2nd ed., 1987.

To use the identification polynucleotides for providing internal identification of a sample, the first step is selection of one identification polynucleotide from each set. For example, if there are 256 different identification polynucleotides in each set, possibly labeled as A1-A256, B1-B256 and C1-C256 if there are three sets, the first sample to be tested might be identified with polynucleotides A1:B1:C1. The next sample could be identified with polynucleotides A1:B1:C2 or A2:B1:C1 and so on through the millions of combinations. A record is kept of the identification polynucleotides used with each sample for later verification.

Once the identification polynucleotides for the sample have been selected, they are added to the sample. Preferably, the identification polynucleotides are added at the time the sample is collected or immediately upon receiving the sample in the testing laboratory to minimize the opportunities for misidentification of the sample.

The amount of identification polynucleotides added to the sample should be comparable to the amount of DNA of the type to be analyzed in the sample. In general, this will mean that from 100 to 200 femtomoles of each identification polynucleotide will be added to each 1 ml of a blood sample, or approximately 1-2 fmol for each 1 µg of patient DNA. Larger amounts may be appropriate in cases where a sample of solid tissue is being analyzed.

After addition of the identification polynucleotides, the sample is treated to sequence both the sample DNA and the identification polynucleotides. This may be performed in parallel reactions, or may involve co-amplification in a single vessel when the amplification conditions for the sample DNA and the identification polynucleotides are compatible. In either case, the identification polynucleotides of all of the sets may be advantageously amplified using a single pair of primers derived from regions of the starting polynucleotide remote from the identification region. These same primers or nested primers are then labeled, for example with fluorescein, and used in the sequencing reaction. The sequencing reaction is preferably performed in an automatic sequencer, for example a Pharmacia A.L.F. Automatic Sequencer. In particular, the same primers used in the original characterization of the polynucleotides may be used in the amplification and sequencing processes.

As illustrated in FIG. 3, the identification regions of each identification polynucleotide are non-overlapping. This arrangement is preferred if the analysis of the identification polynucleotide is made by automated DNA sequencing using the sequencing primer labeled with the same fluorophore for each set. In this case, monochromatic fluorescence emissions will come from all of the sets of identification polynucleotides, and distinguishing between the identification regions requires positional displacement from one another. If, in the alternative, a sequencing primer labeled with a different fluorophore is used to sequence each respective set of identification polynucleotides, then a multicolor fluorescence detector could be used to distinguish between overlapping identification regions from each set of identification polynucleotides, as illustrated in FIG. 5.

The present invention lends itself to the advance preparation of sample collection vessels, i.e. tubes, bottles, slides, etc., containing pre-selected combinations of identification nucleic acids. For example, as shown in FIG. 6, a sample collection tube 1 might be coated on the inside surface with a mixture 2 of identification polynucleotides. A label 3 on the outside of the tube would provide an indication of nature of the identification polynucleotides, for example an identification code as shown in FIG. 6. Preferably, the label is perforated, as shown, with one part being removable. This part of the label is removed and placed on the patient's chart at the time the sample is collected. The identification code which is returned based on the sequenced identification polynucleotides is compared with the number on the removed label to confirm the identification of the sample.

I claim:

1. A method for providing internal identification of a sample containing nucleic acid polymers to be analyzed by nucleic acid sequencing, comprising selecting a plurality of identification polynucleotides, each of said identification polynucleotides being selected from one of a plurality of distinct sets of identification polynucleotides having no common members among the sets, wherein each set contains at least 12 different identification polynucleotides;

adding the selected identification polynucleotides to the sample prior to analysis to form a mixture of the sample and the selected plurality of polynucleotides, wherein the identification polynucleotides do not hybridize with DNA from the sample; and determining the sequence of the identification polynucleotides and the nucleic acid polymers to be analyzed.

2. A method according to claim 1, wherein each set of identification polynucleotides contains from 12 to 420 different identification polynucleotides and one identification polynucleotide is selected from each of 3 to 6 sets.

3. A method according to claim 1, wherein the selected identification polynucleotides are added at the time the sample is collected.

4. A method according to claim 1, wherein all of the identification polynucleotides are derived from a common starting polynucleotide and each identification polynucleotide comprises (a) a primer site which is not homologous with DNA from the sample and which may be the same as or different from the primer site of the other identification polynucleotides; and (b) an identification region having the formula $$-(M-N)_x- \text{ or } -(M-N-N)_x-$$

wherein N represents a nucleotide residue which is the same in the identification polynucleotide as in the starting polynucleotide, M represents a nucleotide residue which may be the same as or different from the starting polynucleotide, with the proviso that at least one M residue in the identification region is different from the starting polynucleotide, and x is an integer from 3 to 20.

5. A method according to claim 4, wherein x is an integer from 4 to 16.

6. A method according to claim 4, wherein x is 10.

7. A method according to claim 1, further comprising the step of amplifying the identification polynucleotides prior to determining the sequence thereof.

8. A method according to claim 7, wherein the identification polynucleotides are co-amplified with the polynucleotides from the sample.

9. A method according to claim 4, wherein from 3 to 6 different identification polynucleotides are added to the sample.

10. A method according to claim 4, wherein 3 different identification polynucleotides are added to the sample.

11. A method according to claim 4, wherein the identification polynucleotides are added at the time the sample is collected.

12. A set of polynucleotides comprising a plurality of distinct polynucleotide species, wherein each polynucleotide species within the set consists of (a) a primer site which is not complementary with human DNA; and (b) an identification region, said identification region containing from 3 to 20 potential variability sites separated from one another by regions which are the same in all polynucleotide species within the set, wherein the identification region of any one polynucleotide species within the set is different from the identification region of all other polynucleotide species within the set as a result of variation of the base at one or more of the potential variability sites, and the remainder of each polynucleotide species within the set is the same as the remainder of all other polynucleotide species within the set.

13. A set of polynucleotides according to claim 12, wherein the identification region of each polynucleotide species within the set has the formula $-(M-N)_x-$ or $-(M-N-N)_x-$ wherein N represents a nucleotide residue which is the same in all polynucleotides species within the set, M represents a potentially variable nucleotide residue which may be different in each polynucleotide species within the set, and x is an integer from 3 to 20.

14. A set of polynucleotides according to claim 13, wherein x is an integer from 4 to 16.

15. A set of polynucleotides according to claim 12, wherein x is 10.

16. A set of nucleic acid polymers according to claim 12, wherein the set comprises at least 20 different individually isolated identification polynucleotides.

17. A method for preparing a set of polynucleotides, said set comprising a plurality of distinct polynucleotide species, comprising the steps of:

(a) selecting a starting polynucleotide having a length of from 100 to 600 base pairs;

(b) inserting the starting polynucleotide into a vector containing an origin of replication;

(c) synthesizing a plurality of modified vectors, one for each member of the set, each modified vector containing a nonmutated sequence fully complementary to a first portion of the starting polynucleotide and a mutated region which is contiguous with the nonmutated sequence such that upon hybridization of the normal region with the first portion of the starting polynucleotide the mutated region is aligned with a second portion of starting polynucleotide, said mutated region having the formula $-(M-N)_x-$ or $-(M-N-N)_x-$ wherein N represents a nucleotide residue which is complementary to the aligned second portion of the starting polynucleotide, M represents a nucleotide residue which may the same as or different from a nucleotide which is complementary to the aligned second portion of the starting polynucleotide with the proviso that at least one M residue in the mutated region is not complementary to the second portion of the starting polynucleotide, and x is an integer from 3 to 20;

(d) cloning the modified vectors in a host organism;

(e) isolating a plurality of organisms, each of said organisms producing one member of the set of polynucleotides; and (f) isolating the polynucleotides produced by said organisms.

18. A method for preparing a set of polynucleotides for use as an internal reference during nucleic acid sequencing of samples from a target organism comprising the steps of (a) selecting a starting polynucleotide having a length of from 100 to 600 base pairs, said starting polynucleotide being selected so as not to hybridize with DNA of the target organism;

(b) inserting the starting polynucleotide into a vector containing an origin of replication;

(c) synthesizing a plurality of modified vectors, one for each member of the set, each modified vector containing a normal region complementary to a first portion of the starting polynucleotide and a mutated region which is contiguous with the normal region such that upon hybridization of the normal region with the first portion of the starting polynucleotide the mutated region is aligned with a second portion of starting polynucleotide, said mutated region having the formula $-(M-N)_x-$ or $-(M-N-N)_x-$ wherein N represents a nucleotide residue which is complementary to the aligned second portion of the starting polynucleotide, M represents a nucleotide residue which may the same as or different from a nucleotide which is complementary to the aligned second portion of the starting polynucleotide with the proviso that at least one M residue in the mutated region is not complementary to the second portion of the starting polynucleotide, and x is an integer from 3 to 20;

(d) cloning the modified vectors in a host organism;

(e) isolating a plurality of organisms, each organism producing one member of the set of polynucleotides; and (f) isolating the polynucleotides produced by said organisms.

19. A method according to claim 18, wherein the set is made up of from 20 to 256 distinct identification polynucleotides.

* * * * *